(12) United States Patent
Turner et al.

(10) Patent No.: US 9,139,939 B2
(45) Date of Patent: Sep. 22, 2015

(54) TREATED LAMINATES

(75) Inventors: Robert Haines Turner, Cincinnati, OH (US); Jonathan Aaron Lu, Cincinnati, OH (US); Antonius Lambertus De Beer, Loveland, OH (US); Lisa Marie Reynolds, Hamilton Twp., OH (US); Randall Allen Myers, Fairfield, OH (US); Walter Douglas Daniels, Maineville, OH (US); David D. Newkirk, Greer, SC (US)

(73) Assignee: The Procter & Gamble Company, Cincinnati, OH (US)

( * ) Notice: Subject to any disclaimer, the term of this patent is extended or adjusted under 35 U.S.C. 154(b) by 744 days.

(21) Appl. No.: 13/005,133

(22) Filed: Jan. 12, 2011

(65) Prior Publication Data

US 2011/0282312 A1 Nov. 17, 2011

Related U.S. Application Data

(60) Provisional application No. 61/294,248, filed on Jan. 12, 2010.

(51) Int. Cl.

| | |
|---|---|
| *A61F 13/15* | (2006.01) |
| *A61F 13/513* | (2006.01) |
| *D04H 3/14* | (2012.01) |
| *A61F 13/514* | (2006.01) |
| *B32B 5/24* | (2006.01) |
| *B32B 25/10* | (2006.01) |
| *D04H 13/00* | (2006.01) |
| *A61F 13/511* | (2006.01) |

(52) U.S. Cl.
CPC .............. *D04H 3/14* (2013.01); *A61F 13/5148* (2013.01); *B32B 5/24* (2013.01); *B32B 25/10* (2013.01); *D04H 13/00* (2013.01); *A61F 13/51113* (2013.01); *Y10T 428/24802* (2015.01); *Y10T 442/659* (2015.04); *Y10T 442/674* (2015.04)

(58) Field of Classification Search
CPC . A61F 13/51; A61F 13/513; A61F 13/51305; A61F 13/51113
USPC ......... 604/367, 378, 385.101, 385.16, 385.22
See application file for complete search history.

(56) References Cited

U.S. PATENT DOCUMENTS

| | | | |
|---|---|---|---|
| 3,595,731 A | 7/1971 | Davies et al. | |
| 4,770,925 A | 9/1988 | Uchikawa et al. | |
| 5,162,074 A | 11/1992 | Hills | |
| 5,242,436 A * | 9/1993 | Weil et al. ................ | 604/385.29 |
| 5,344,297 A | 9/1994 | Hills | |
| 5,466,410 A | 11/1995 | Hills | |
| 5,529,665 A | 6/1996 | Kaun | |
| 5,607,760 A * | 3/1997 | Roe .............................. | 442/375 |
| 5,804,286 A | 9/1998 | Quantrille et al. | |
| 5,814,349 A | 9/1998 | Geus et al. | |
| 5,869,172 A | 2/1999 | Caldwell | |
| 6,288,144 B1 | 9/2001 | Roberts et al. | |
| 6,352,700 B1 | 3/2002 | Luu et al. | |
| 6,417,121 B1 | 7/2002 | Newkirk et al. | |
| 6,417,122 B1 | 7/2002 | Newkirk et al. | |

(Continued)

FOREIGN PATENT DOCUMENTS

WO WO 9932706 * 1/1999 ............ D06M 15/03

*Primary Examiner* — Jacqueline Stephens
(74) *Attorney, Agent, or Firm* — Sarah M. DeCristofaro; Charles R. Ware

(57) ABSTRACT

Methods of treating laminates, treated laminates, and articles with treated laminates.

46 Claims, 5 Drawing Sheets

(56) References Cited

U.S. PATENT DOCUMENTS

| | | |
|---|---|---|
| 6,420,285 B1 | 7/2002 | Newkirk et al. |
| 7,422,712 B2 | 9/2008 | Delucia et al. |
| 7,491,770 B2 | 2/2009 | Autran |
| 2002/0119720 A1 | 8/2002 | Arora et al. |
| 2003/0092598 A1* | 5/2003 | Gardner et al. ............... 510/513 |
| 2004/0033270 A1 | 2/2004 | Kropf et al. |
| 2004/0116018 A1 | 6/2004 | Fenwick et al. |
| 2005/0096623 A1* | 5/2005 | Nhan et al. ............... 604/385.22 |
| 2007/0088304 A1* | 4/2007 | Sakano et al. ........... 604/385.19 |

* cited by examiner

TREATED LAMINATES

CROSS-REFERENCE TO RELATED APPLICATION

This application claims priority to U.S. provisional application 61/294,248, filed Jan. 12, 2010, which is hereby incorporated by reference.

TECHNICAL FIELD

This disclosure relates to surface-treated non-woven fabrics, as well as related laminates, products, machines, and methods.

BACKGROUND

Non-woven fabrics produced from spun polymer materials are used in a variety of different applications. For example, such non-woven fabrics can be employed as the cover sheet or back sheet for disposable diapers or sanitary products. There is considerable interest in making disposable diapers more comfortable and better fitting to the baby. An important part of the diaper comfort is the softness of the non-woven fabrics used to make the diaper, including the diaper top sheet, barrier leg cuffs, and in some advanced designs, the fabric laminated to the back sheet film. In addition, in some diaper designs, a high degree of fabric elongation is needed to cooperate with elastic components for achieving a soft comfortable fit.

Also, contamination due to fiber buildup is a major problem encountered during roll good conversion of nonwovens through high strain/high shear processes, particularly with nonwovens having bicomponent fibers and particularly in processes which involve the use of adhesive to laminate nonwovens to other roll good substrates as contact pressure can force the adhesive through the porous web onto the converting equipment surfaces which in turn continually attracts loose fibers from the web itself.

SUMMARY

This disclosure is based on the unexpected discovery that adding a small amount of a composition containing a surface-modifying agent such as a polysiloxane polymer on a surface of a non-woven fabric significantly improves the abrasion resistance of the fabric during the manufacturing of a personal care product (e.g., a diaper) using the fabric In one aspect, this disclosure features a non-woven fabric that includes a plurality of continuous fibers and a composition disposed on a surface of at least some of the plurality of continuous fibers. At least some of the plurality of continuous fibers are bonded to each other. The composition includes a surface-modifying agent (e.g., an agent that lubricates the fabric). When a side of a sample of the fabric is subjected to a Sutherland Ink Rub test (ASTM: D-5264) using a 320 grit sandpaper and an one pound weight, the sample has a weight loss of at most 0.1 mg/cm$^2$. In some embodiments, each fiber includes a first polymer and a second polymer different from the first polymer.

In another aspect, this disclosure features a non-woven fabric that includes a plurality of continuous fibers and a composition disposed on a surface of at least some of the fibers. At least some of the plurality of continuous fibers are bonded to each other. The composition includes a surface-modifying agent (e.g., an agent that lubricates the fabric). In some embodiments, each fiber includes a first polymer and a second polymer different from the first polymer.

In another aspect, this disclosure features a non-woven fabric that includes a plurality of continuous fibers and a composition disposed on a surface of at least some of the fibers. At least some of the plurality of continuous fibers are bonded to each other. The composition includes a surface-modifying agent. In a Sutherland Ink Rub test, the fabric loses its weight due to abrasion at least 25% less than the weight lost by a fabric without including the composition comprising the surface-modifying agent. In some embodiments, each fiber includes a first polymer and a second polymer different from the first polymer.

In another aspect, this disclosure features a non-woven fabric for use in a back sheet. The fabric includes a plurality of continuous fibers and a composition disposed on a surface of at least some of the fibers. At least some of the plurality of continuous fibers are bonded to each other. The composition includes a surface-modifying agent. The surface-modifying agent includes a polysiloxane homopolymer or copolymer. In some embodiments, each fiber includes a first polymer and a second polymer different from the first polymer.

In another aspect, this disclosure features a non-woven fabric that includes a composition disposed on a surface of at least some of the plurality of continuous fibers. The composition includes a surface-modifying agent. The fabric is configured to pass the Shear Hang Time test of the present disclosure for at least 60 minutes.

In another aspect, this disclosure features a nonwoven fabric that includes a composition disposed on a surface of at least some of the plurality of continuous fibers. The composition includes a surface-modifying agent. The fabric is configured to have a creep of 12 millimeters or less when subjected to the Side Creep test of the present disclosure.

In another aspect, this disclosure features a non-woven laminate that includes one of the fabrics described above and a layer attached to the fabric.

In another aspect, this disclosure features a personal care product (e.g., a disposable personal product) that includes a non-woven fabric or laminate described above.

In another aspect, this disclosure features a method that includes forming a non-woven fabric containing a plurality of continuous fibers, and disposing a composition (e.g., an aqueous solution or emulsion) on a surface of at least a portion of the fabric. Each fiber includes a first polymer and a second polymer different from the first polymer. The composition includes a surface-modifying agent (e.g., an agent that lubricates the fabric). When a side of a sample of the fabric is subjected to a Sutherland Ink Rub test using a 320 grit sandpaper and an one pound weight, the sample has a weight loss of at most 0.1 mg/cm$^2$.

In another aspect, this disclosure features a method that includes forming a nonwoven fabric containing a plurality of continuous fibers, and disposing a composition on a surface of at least a portion of the fabric. Each fiber includes a first polymer and a second polymer different from the first polymer.

In another aspect, this disclosure features a method that includes forming a non-woven fabric containing a plurality of continuous fibers, and disposing a composition on a surface of at least a portion of the fabric. Each fiber includes a first polymer and a second polymer different from the first polymer. The composition includes a surface-modifying agent (e.g., an agent that lubricates the fabric). In a Sutherland Ink Rub test, the fabric loses its weight due to abrasion at least 25% less than the weight lost by a fabric without including the composition comprising the surface-modifying agent.

In another aspect, this disclosure features a method that includes forming a non-woven fabric containing a plurality of continuous fibers, and disposing a composition on a surface of at least a portion of the fabric to form a back sheet. Each fiber includes a first polymer and a second polymer different from the first polymer. The composition includes a surface-modifying agent. The surface-modifying agent includes a polysiloxane homopolymer or copolymer.

In another aspect, this disclosure features a machine for converting absorbent articles. The machine includes a contact surface configured to contact a web, in which at least a portion of the contact surface includes a composition that includes a surface-modifying agent.

Embodiments can include one or more of the following optional features.

When a side of a sample of the fabric is subjected to a Sutherland Ink Rub test using a 320 grit sandpaper and an one pound weight, the sample has a weight loss of at most 0.1 mg/cm$^2$.

The surface-modifying agent includes a polysiloxane (e.g., poly(dialkylsiloxane) such as poly(dimethylsiloxane)) homopolymer or copolymer. For example, the composition includes a poly(dialkylsiloxane-co-alkylene glycol) (e.g., poly(dimethylsiloxane-co-alkylene glycol)).

The polysiloxane homopolymer or copolymer is at least 50% (e.g., at least 70%) of the total weight of the composition.

The composition further includes an emulsifier for forming an emulsion, which can include an alkoxy polyethoxy ethanol, a polyalkylene glycol polymer, or an alkyl monoether of a polyalkylene glycol polymer.

The composition is at least 0.01% and at most 0.5% (e.g., at most 0.1% or at least 0.04%) by weight of the total weight of the fabric. In various embodiments, the composition can be: i) less than or equal to 0.45% of the total weight of the fabric and greater than or equal to 0.0225% of the total weight of the fabric; ii) less than or equal to 0.335% of the total weight of the fabric and greater than or equal to 0.045% of the total weight of the fabric; iii) less than or equal to 0.225% of the total weight of the fabric and greater than or equal to 0.1% of the total weight of the fabric; and/or iv) less than or equal to 0.18% of the total weight of the fabric and greater than or equal to 0.125% of the total weight of the fabric.

While embodiments of the present disclosure refer to bicomponent fibers, it is contemplated that embodiments of the present disclosure can also be applied to various kinds of fibers with a single component (e.g., a single component formed by multiple constituents such as a blend of polymers), or with more than two components.

Each fiber includes a mixture of the first and second polymers.

Each fiber includes a first polymer domain and a second polymer domain, the first polymer domain includes the first polymer and the second polymer domain includes the second polymer.

The first polymer domain is configured as a core and the second polymer domain is configured as a sheath. The core and the sheath have a weight ratio ranging from 90:10 to 10:90 (e.g., 80:20 to 20:80 or 75:25 to 65:35).

The first polymer is a polypropylene polymer and the second polymer is a polyethylene polymer.

The plurality of continuous fibers has an average diameter of at most 25 μm.

The fabric has an elongation at peak load in at least one of the machine direction and the cross-machine direction of at least 70 percent when tested via WSP 110.4 (B).

The plurality of continuous fibers are spunbonded fibers.

The fabric includes two or more layers (e.g., two, three, four, five, or more layers). Each of the two or more layers contains spunbonded fibers. In some embodiments, at least one of the two or more layers includes spunbonded fibers and at least another of the two or more layers can contain meltblown fibers.

The fabric further includes an adhesive (e.g., a hot-melt adhesive).

The fabric is configured to pass the Shear Hang Time test of the present disclosure for at least 90 minutes (e.g., at least 120 minutes, at least 150 minutes, or at least 180 minutes).

The fabric is configured to have a creep of 11 millimeters or less (e.g., 10 millimeters or less, 9 millimeters or less, 8 millimeters or less, 7 millimeters or less, or 6 millimeters or less) when subjected to the Side Creep test of the present disclosure.

The layer in the laminate includes a second non-woven fabric (e.g., a meltblown fabric) or a film (e.g., an extensible film or an elastic film).

The fabric in the laminate is permanently elongated by mechanical stretching.

In a Sutherland Ink Rub test, the fabric loses its weight due to abrasion at least 25% less than the weight lost by a fabric without including the composition comprising a polysiloxane homopolymer or copolymer.

The personal care product (e.g., a disposable personal care product) can be, for example, a diaper (e.g., a pants-type diaper, a training pant diaper, a tape-type diaper, or a mechanical fastener type diaper), an incontinence pad, an incontinence brief, a sanitary napkin, a bandage, or a sliding sheet (e.g., for transferring a patient from one bed to another bed).

The method includes, in the forming a non-woven fabric step, melting the first and second polymers, and extruding the first melted polymer through a first extruding device and the second melted polymer through a second extruding device to form the extruded fibers. The forming a non-woven fabric step can further include disposing the extruded fibers on a collector. After disposing the extruded fibers on the collector, the method can further include forming bonds (e.g., by mechanical needling, thermal bonding, ultrasonic bonding, or chemical bonding) between at least some of the plurality of continuous fibers in the forming a non-woven fabric step.

The method further includes attaching a layer (e.g., a meltblown fabric or a film such as an extensible or elastic film) to the fabric after disposing the composition, thereby forming a non-woven laminate. The laminate can then be stretched (e.g., by a ring roll) to form a disposable personal care product.

The method further includes applying an adhesive (e.g., a hot-melt adhesive) to the fabric after the composition is disposed on the surface of at least a portion of the fabric.

The composition to be disposed on the surface of at least a portion of the fabric includes an aqueous solution or emulsion containing the surface-modifying agent. Such a composition is disposed on the surface of at least a portion of the fabric by using a kiss roll or by another method of coating the surface such as spraying.

In various embodiments, a machine used to process laminates of the present disclosure, can include a roller, a guide, a blade, or ring-rolls and one or more portions of contact surfaces on these machine elements can be treated with the surface modifying composition.

Embodiments can provide one or more of the following advantages.

Treating a surface of at least some of the multicomponent fibers in a non-woven fabric with even a small amount (e.g., at most 0.04% by weight of the fabric) of the composition described above can significantly improve fiber abrasion resistance and reduce fiber breakage or fiber pull-out when exposed to an abrasive surface and/or mechanical force upon stretching (e.g., during manufacturing of a personal care product using the fabric). Such a fabric can be used to manufacture a back sheet for a diaper without contaminating the stretching machine (e.g., a ring rolling machine) with broken fibers during manufacturing.

The addition of the surface-modifying composition improves the processability of the non-woven fabric, for example, by continuously transferring the surface-modifying agent from the non-woven fabric to processing equipment which prevents migration of an adhesive used to laminate the non-woven fabric through the fabric to the processing equipment and thus minimize buildup of loose fibers on the equipment.

A product that includes a non-woven fabric treated with a surface-modifying agent at the levels described herein can maintain good functionality since the low level of the agent is not expected to interfere with chemical/mechanical bonding interactions in the fabric. Accordingly, a non-woven fabric treated with a surface modifying agent at the levels described herein should perform well when tested for elastic creep or shear hang time as described herein.

Other features, objects, and advantages of the invention will be apparent from the description and drawings, and from the claims.

DETAILED DESCRIPTION

Figure 1:
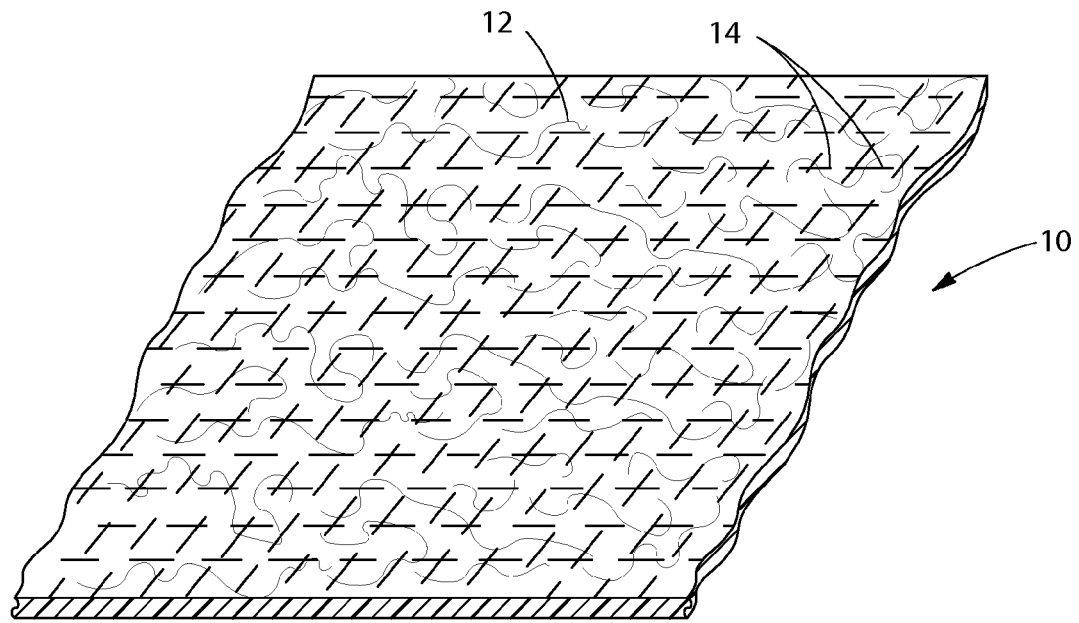
FIG. 1 is a prospective view of a spunbonded non-woven fabric formed of a plurality of multicomponent fibers.
Figure 2:
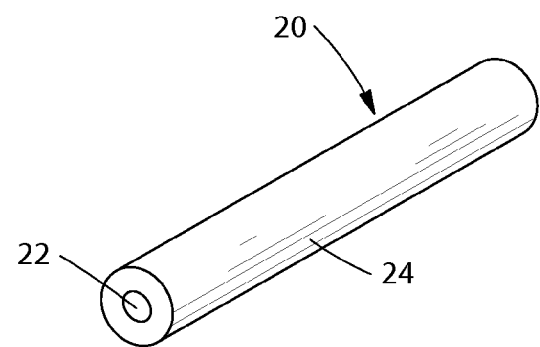
FIG. 2 is a prospective view of a multicomponent fiber.

FIG. 1 is a perspective view of a spunbonded non-woven fabric 10 formed of a plurality of continuous multicomponent fibers 12, at least some (e.g., all) of which are bonded with each other through a plurality of intermittent bonds 14. As used herein, the term "non-woven fabric" refers to one or more layers of continuous fibers that are bonded together. The term "continuous fiber" mentioned herein refers to filaments. The filaments are fibers that typically extend through a major part of the entire length or width of the non-woven fabric, as opposed to a staple fiber which has a distinct length (e.g. 1.5 inch) independent of and different from the length or width of a non-woven fabric. The non-woven fabric can be formed in a continuous process where a continuous fiber or filament is extruded and provided in the fabric. The non-woven fabric can then be cut to a particular size (having a distinct length and width) and the continuous fiber or filament would generally have a length equal to or greater than the length or width of the nonwoven fabric. An exemplary multicomponent fiber 12 is illustrated in FIG. 2 and is discussed in more detail below. In general, non-woven fabric 10 includes a planar structure that is relatively flexible and porous. While embodiments of the present disclosure refer to nonwoven fabrics, it is contemplated that embodiments of the present disclosure can also be applied to various other types of fibrous webs.

In some embodiments, at least some of the multicomponent fibers 12 (e.g., all of the fibers) in non-woven fabric 10 include a surface-modifying composition (e.g., a composition containing a surface-modifying agent) on their surface. For example, the composition can be provided on a surface of the fabric and the fibers forming that surface can include the composition. In general, the composition includes a surface-modifying agent and optionally an emulsifier. The surface modifying agent can be a surfactant or a lubricant (e.g., an agent that lubricates non-woven fabric 10).

Without wishing to be bound by theory, it is believed that the surface-modifying agent can perform one or more of the following functions: lubricating the nonwoven fabric to protect it during stretching through ring rolling, improving abrasion resistance of the fabric, reducing fiber breakage or fiber pullout upon stretching, removing debris of damaged fibers and adhesive from the surface of the ring roll, and preventing migration of the adhesive at the fabric-film interface in a laminate to the surface of a ring roll through the fabric, thereby minimizing contamination of the surface of the ring roll. Thus, any material providing one or more of these functions can be useful as a surface modifying agent described herein. So, the surface modifying agent modifies the treated surface, by virtue of its presence on the surface, as described above.

The surface-modifying agent can be a polysiloxane polymer (e.g., a polysiloxane homopolymer or copolymer). For example, the polysiloxane polymer can be a poly(dialkylsiloxane) homopolymer (e.g., poly(dimethylsiloxane)) or a poly(dialkylsiloxane) copolymer (e.g., poly(dimethylsiloxane-co-alkylene glycol)). Poly(dialkylsiloxane) homopolymers and copolymers are well known in the art, such as those described in U.S. Pat. Nos. 4,169,905; 4,324,720; and 5,811,482. In some embodiments, the polysiloxane polymer can be at least 50% (e.g., at least 60%, at least 70%, at least 80%, or at least 90%) or at most 100% (e.g., at most 95%, at most 90%, at most 85%, at most 75%, at most 65%; or at most 55%) of the total weight of the surface-modifying composition in a dried form (e.g., without a solvent such as water).

In some embodiments, a polysiloxane copolymer can include a hydrophobic monomer unit (e.g., a siloxane monomer unit) and a hydrophilic monomer unit (e.g., an alkylene glycol monomer unit). The hydrophobicity of such a polysiloxane copolymer can vary depending on the molar ratio between the hydrophobic and hydrophilic monomer units in the copolymer. In some embodiments, the polysiloxane copolymer includes a sufficient amount of hydrophobic monomer units to maintain the hydrophobicity of the surface of non-woven fabric 10 and a sufficient amount of hydrophilic monomer units so that the copolymer can be readily emulsified in water for easy application (e.g., via a kiss roll). For example, to manufacture the back sheet of a diaper (which typically requires a sufficiently high hydrophobicity), the surface-modifying composition on the surface of non-woven fabric 10 can include a hydrophobic polysiloxane polymer in which the molar ratio between the hydrophobic and hydrophilic monomer units is at least 2:1 (e.g., at least 3:1, at least 4:1, at least 5:1, or at least 6:1) or a hydrophobic polysiloxane polymer having a hydrophilic-lipophilic balance (HLB) value of at most 10 (e.g., at most 8, at most 6, at most 5, at most 4, at most 2, or at most 1). In various embodiments, a nonwoven fabric can also be treated with a surface-modifying agent of the present disclosure, such that the non-woven fabric is rendered hydrophilic.

In some embodiments, the surface-modifying agent can be a lubricant, such as those typically used in manufacturing a synthetic fiber. Examples of such lubricants include refined white oil, or mono- or di-esters of aliphatic C8-C18 branched or straight chain, saturated or unsaturated, carboxylic acids with a monohydric aliphatic C3-C18, branched or straight chain alcohol. The esters generally have a viscosity of less than 15-40 centipoises over a relative humidity range of 10-100% when measured at 35° C. Exemplary esters include butyl stearate, isobutyl palmitate, octyl stearate, isopropyl myristate, isocetyl stearate, dioctyl sebacate, trimethylolpropane tripelargonate, pentaerythritol tetrapelargonate, mineral oil, coconut oil, corn oil, and sperm oil. Other examples have been described, for example, in U.S. Pat. No. 3,997,450.

In some embodiments, the surface-modifying agent can be a saturated fatty acid or an unsaturated fatty acid (e.g., an unsaturated omega-9 fatty acid such as a ricinoleic acid).

In general, the emulsifier in the surface-modifying composition is used to make the surface-modifying agent (e.g., a polysiloxane polymer) dispersible in a solvent (e.g., an aqueous solvent). Examples of suitable emulsifiers include an alkoxy polyethoxy ethanol, a polyalkylene glycol polymer, and an alkyl monoether of a polyalkylene glycol polymer. In some embodiments, the emulsifier can be at most 50% (e.g., at most 40%, at most 30%, at most 20%, at most 10%, at most 7%, or at most 5%) or at least 0% (e.g., at least 3%, at least 5%, at least 10%, at least 15%, or at least 25%) of the total weight of the surface-modifying composition in a dried form (e.g., without a solvent such as water). In some embodiments, the surface-modifying composition does not include the emulsifier. For example, when the surface-modifying agent (e.g., a polysiloxane polymer) is soluble in the solvent (e.g., an organic solvent) used in the composition, the composition does not need to include an emulsifier.

In some embodiments, the surface-modifying agent can be included in another composition, such as a solution of ink for printing on a non-woven material. In various embodiments, the surface modifying composition can be clear or opaque.

In some embodiments, the surface-modifying composition in a dried form (e.g., without a solvent such as water) can include 70%-90% by weight of a poly(dimethylsiloxane-co-alkylene glycol) copolymer and 10%-30% by weight of a polyalkylene glycol, A commercially available example of such a composition is SILWET L-7602 from Momentive Performance Materials (Albany, N.Y.). In some embodiments, the surface-modifying composition in a dried form can include at least 80% by weight of a poly(dimethylsiloxane) homopolymer and 3%-7% by weight of an alkoxy polyethoxy ethanol. A commercially available example of such a composition is LUROL 3503 from Goulston Technologies, Inc, (Monroe, N.C.).

In some embodiments, the surface-modifying composition can also include a solvent to form a solution or an emulsion to facilitate application of the active ingredients in the composition onto the surface of non-woven fabric 10. The solvent generally does not substantially dissolve the polymers used in the fibers to be coated with the surface-modifying composition. Examples of suitable solvent include water and organic solvents (e.g., polar organic solvents such as alcohols). For example, before the surface-modifying composition is applied onto a surface of non-woven fabric 10, it can be an aqueous emulsion (e.g., containing a surface-modifying agent dispersed in water) or an aqueous solution (e.g., containing a surface-modifying agent dissolved in a mixture of water and an alcohol). As another example, the surface-modifying composition can be an organic solution containing a surface-modifying agent dissolved in an organic solvent (e.g., an alcohol) before the composition is applied onto a surface of non-woven fabric 10.

The amount of the surface-modifying composition in a dried form (e.g., without a solvent such as water) on non-woven fabric 10 can vary as desired. In general, the amount of the surface-modifying composition is sufficiently large to improve fiber abrasion resistance and sufficiently small to reduce its interference with the adhesion properties of fabric 10 and to reduce manufacturing costs. Specifically, if the amount of the surface-modifying composition is too small, it may not effectively improve fiber abrasion resistance of fabric 10. On the other hand, if the amount of the surface-modifying composition is too large, it may increase manufacturing costs, and reduce the adhesion between fabric 10 and another layer (e.g., an extensible polyolefin film) in the final personal care product (e.g., a diaper). The amount of the surface-modifying composition can also vary based on the type and amount of the surface-modifying agent and emulsifier used. In some embodiments, the surface-modifying composition in a dried form can be at most 0.5% (e.g., at most 0.3%, at most 0.15%, at most 0.1%, at most 0.08%, at most 0.06%, at most 0.04%, or at most 0.02%) or at least 0.005% (e.g., at least 0.01%) by weight of the total weight of fabric 10. Unexpectedly, treating a surface of at least some of the multicomponent fibers 12 in non-woven fabric 10 with even a small amount (e.g., at most 0.04% by weight of the fabric) of the surface-modifying composition described above in a dried form can significantly improve fiber abrasion resistance and reduce fiber breakage or fiber pull-out when exposed to an abrasive surface and/or mechanical force upon stretching (e.g., during manufacturing of a personal care product using the fabric). Such a fabric can be used to manufacture a back sheet or side panel for a diaper without contaminating the stretching machine (e.g., a ring rolling machine) with broken fibers during manufacturing. The surface-modifying composition described above is particularly useful to fabrics made from multicomponent fibers (e.g., those having a sheath/core structure) compared to fabrics made of a single-component fibers as one of the polymer compositions used in the multicomponent fibers (e.g., the sheath in a sheath/core structure) tends to break or abrade off relatively easily upon stretching.

Fiber abrasion resistance of non-woven fabric 10 can be characterized by the weight loss of the fabric in a Sutherland Ink Rub test. The Sutherland Ink Rub test is generally described in ASTM 5264, and more specifically described in the Example section below and in, for example, U.S. Pat. No. 7,491,770 and U.S. Application Publication No. 2002/0119720. For example, when a side of a sample of non-woven fabric 10 is subjected to a Sutherland Ink Rub test using a 320 grit sandpaper and an one pound weight, the sample can have a weight loss of at most 0.1 mg/cm$^2$ (e.g., at most 0.09 mg/cm$^2$, at most 0.08 mg/cm$^2$, at most 0.07 mg/cm$^2$, at most 0.06 mg/cm$^2$, at most 0.05 ing/cm$^2$, or at most 0.04 mg/cm$^2$) in a Sutherland Ink Rub test. In some embodiments, in a Sutherland Ink Rub test, non-woven fabric 10 loses its weight due to abrasion at least 15% (e.g., at least 20% or at least 25%) less than the weight loss by a fabric without including the composition containing a surface modifying agent.

Without wishing to be bound by theory, it is believed that the addition of the surface-modifying composition improves the processability of the non-woven fabric. For example, the portions of the processing equipment that contact the treated non-woven fabric during the process to converting to diapers can continuously accept the surface-modifying agent transferred from the fabric, such that, during the converting process, the contacting portions do not acquire adhesive or fibers transferred from the fabric. These portions may be made of steel, aluminum, tungsten carbide, other metallic alloys, or other materials. In various embodiments, the portions of the processing equipment that contact the treated non-woven fabric can also be coated with an additional coating, such as a permanent, compacted, and non-conductive coating derived from nickel oxide polymers. As an example, the coating could be a NEDOX coating available from the Magnaplate Company of Linden, N.J.

The surface-modifying composition described above can be distributed continuously or non-continuously (e.g., when the amount of the composition is small) on the surface of at least a portion of the fabric and thus on the surface of at least some of the multicomponent fibers in non-woven fabric 10. When the surface-modifying composition is distributed non-continuously on the surface of the fabric, certain areas of the surface are not covered by the composition.

To manufacture a personal care product, non-woven fabric 10 can include multicomponent fibers 12 with a suitable denier (i.e., linear mass density) to balance the potentially conflicting requirements of (i) softness, (ii) barrier capability with respect to both urine and adhesives, (iii) formation, strength, and extensibility during stretching (e.g., by ring rolling), and (iv) the economics of fiber spinning. For example, multicomponent fibers 12 can have a linear mass density of at most 5 denier per filament (e.g., at most 4 denier per filament, at most 3 denier per filament, or at most 2 denier per filament) or at least 0.5 denier per filament (e.g., at least 1 denier per filament, at least 1.5 denier per filament, or at least 2 denier per filament). Preferably, multicomponent fibers 12 can have a linear mass density of between 1 and 5 denier per filament (e.g., between 1.5 and 4 denier per filament, or between 2 and 3 denier per filament). In some embodiments, non-woven fabric 10 includes fibers having a smaller linear mass density compared to the carpet fabrics used for producing carpets. Such a non-woven fabric 10 typically includes multicomponent fibers 12 with a relatively small average diameter. For example, multicomponent fibers 12 can have an average diameter of at most 25 μm (e.g., at most 20 μm, at most 15 μm, or at most 10 μm) or at least 5 μm (e.g., at least 8 μm, at least 13 μm, or at least 18 μm).

In general, non-woven fabric 10 can have a suitable basis weight to balance the requirements of (i) softness, (ii) barrier capability, (iii) formation, strength, and extensibility during stretching, and (iv) cost. For example, non-woven fabric 10 can have a basis weight of 8-40 g/m (e.g., 10-30 g/m$^2$ or 12-25 g/m$^2$) when used as a top sheet, back sheet, or side-panel in a diaper.

Non-woven fabric 10 can include one layer of fibers or more than one layer (e.g., two, three, four, five, or more layers) of fibers. For example, when fabric 10 includes more than one layer, each layer can contain spunbonded (S) fibers to form, for example, a S, SS, or SSS type of fabrics. In various embodiments, when the non-woven fabric 10 is treated with a surface modifying composition, as described herein, the fabric may be formed with one or more layers of spunbonded fibers and without the need for another kind of fibers, such as meltblown fibers. So, in various embodiments, a laminate of the present disclosure may have a nonwoven material with only spunbonded fibers. The ability to use spunbonded fibers without meltblown fibers offers several potential advantages, including better clarity graphics on the spunbonded fibers, and better breathability.

The breathability of laminates of the present disclosure can be evaluated by measuring the air permeability of the laminates. As used herein, air permeability is measured in meters per minute by test method GCAS 95059095 with the following parameters: test dp=125 PA and test area=38 cm$^2$. In various embodiments, laminates of the present disclosure can have an air permeability of 70-200 meters per minute, 90-200 meters per minute, 110-200 meters per minute, or 130 meters per minute.

Non-woven fabric 10 can also include more than one layer of fabrics in which at least one layer contain fibers formed by a method different from that used to form the fibers in another layer. For example, when fabric 10 includes more than one layer of fibers, at least one layer can include spunbonded fibers and at least another layer can include meltblown (M) fibers. In such a fabric, the layers containing spunbonded fibers and the layers containing meltblown fibers can be arranged in any order as desired. For examples, the layers can be arranged in the order of SM, SMS, SMMS, or SSMMS. In such embodiments, spunbonded and meltblown fibers can be formed by using materials known in the art. For example, spunbonded fibers can be multicomponent fibers 12 described herein and meltblown fibers can be formed by using a polyolefin (e.g., polypropylene, polyethylene, or copolymers thereof) or a polyester (e.g., PET). The meltblown fibers can be single component fibers or multicomponent fibers. In some embodiments, the meltblown fibers can have an average diameter (e.g., about 3-6 μm) smaller than the spunbonded fibers.

Non-woven fabric 10 can be made by methods well known in the art, such as spunbonding. Spunbonded non-woven fabric 10 can be produced by a known spunbond process (e.g., a Reifenhauser-3 or Reifenhauser-4 process). For example, after the polymers for making multicomponent fibers are melted, the molten polymers can be extruded from an extruding device. The molten polymers can then be directed into a spinneret with composite spinning orifices and spun through this spinneret to form multicomponent fibers (e.g., continuous multicomponent fibers). The fibers can subsequently be quenched (e.g., by cool air), attenuated mechanically or pneumatically (e.g., by a high velocity fluid), and collected in a random arrangement on a surface of a collector (e.g., a moving substrate such as a moving wire or belt) to form a non-woven web. In some embodiments, a plurality of spinnerets with different quenching and attenuating capability can be used to place one or more (e.g., two, three, four, or five) layers of multicomponent spunbonded fibers 12 on a collector to form fabrics containing one or more layers of spunbonded fibers (e.g., a S, SS, or SSS type of fabric). In some embodiments, one or more layers of meltblown fibers can be inserted between the layers of the above-described spunbonded fibers to form fabrics containing both spunbonded and meltblown fibers (e.g., a SMS, SMMS, or SSMMS type of fabric).

A plurality of intermittent bonds 14 can subsequently be formed between at least some of the fibers (e.g., all of the fibers) to form a unitary, coherent, non-woven fabric. Bonds 14 can be formed by a suitable method such as mechanical needling, thermal bonding, ultrasonic bonding, or chemical bonding. Bonds 14 can be covalent bonds (e.g., formed by chemical bonding) or physical attachments (e.g., formed by thermal bonding). Preferably, bonds 14 are formed by thermal bonding. For example, bonds 14 can be formed by known thermal bonding techniques, such as a process using calender rolls with a point bonding pattern (e.g., continuous or discontinuous patterns). Bonds 14 can cover between 6 and 40 percent (e.g., between 8 and 30 percent or between 22 and 28 percent) of the total area of non-woven fabric 10. Without wishing to be bound by theory, it is believed that forming bonds in fabric 10 within these percentage ranges allows elongation throughout the entire area of fabric 10 upon stretching while maintaining the strength and integrity of the fabric.

After bonds 14 are formed, the surface-modifying composition described above can be applied onto the surface of at least some of the multicomponent fibers in non-woven fabric 10 by methods well known in the art. For example, when the surface-modifying agent and/or emulsifier is a liquid, the surface-modifying composition can be directly applied to the surface by a known coating method (e.g., spray coating, solution coating, or print coating) without including a solvent. Alternatively, when the surface-modifying agent and/or emulsifier is a liquid, they can be first diluted in a solvent (e.g., an aqueous or organic solvent) to form a solution, emulsion, or dispersion, applied onto the surface of at least some of the multicomponent fibers in non-woven fabric 10 by a known coating method (e.g. by using a kiss roll or by another application method such as spraying), and then dried to form the surface-modifying composition. When the surface-modifying agent and/or emulsifier is a solid, they can be first dissolved or dispersed in a solvent (e.g., an aqueous or organic solvent) to form a solution, emulsion, or dispersion, which can then be applied to the surface of at least some of the multicomponent fibers in non-woven fabric 10 to form the surface-modifying composition. The surface-modifying agent and/or emulsifier can also be formed into a foam, which can then be applied to the surface of at least some of the multicomponent fibers in non-woven fabric 10.

Alternatively, the surface-modifying composition can be applied onto the surface of at least some of the multicomponent fibers in non-woven fabric 10 before multicomponent fibers 12 are bonded to form bonds 14. For example, one can deposit extruded fibers on a collector, apply the surface-modifying composition as a solution or emulsion onto the surface of extruded fibers, dry the solution or emulsion, and then form bonds between at least some of the multicomponent fibers thus formed to form a non-woven fabric. As another example, non-woven fabric 10 can be made by (1) misting a solution containing the surface-modifying agent and/or emulsifier into the quenching air in the quench zone after multicomponent fibers 12 are formed by spinning, (2) drying the resulting multicomponent fibers 12 during a pneumatically attenuation process, (3) depositing the fibers thus formed on a collector, and then (4) forming bonds between at least some of the multicomponent fibers to produce a non-woven fabric 10.

In some embodiments, the surface-modifying agent can also be formed on the surface of at least some of the multicomponent fibers in non-woven fabric 10 after fabric 10 is attached to another layer (e.g., a meltblown fabric or a film) by an adhesive to form a laminate. In other embodiments, the surface-modifying; agent can be included in a masterbatch material from which the fibers of the non-woven fabric are created.

After the surface-modifying composition is formed on non-woven fabric 10, the fabric can be used in the manufacturing of a personal care product (e.g., a diaper) by methods known in the art (e.g., by using a ring rolling machine).

FIG. 2 illustrates an exemplary multicomponent fiber 20 that can be used to manufacture non-woven fabric 10 shown in FIG. 1. Multicomponent fiber 20 includes a first polymer domain 22 and a second polymer domain 24. As used herein, the term "domain" refers to a discrete structured component, as opposed to a component randomly dispersed in one or more other components. For example, a polymer domain mentioned herein can be arranged in a distinct zone across the cross section of a multicomponent fiber and extends continuously along the length of the fiber. In some embodiments, multicomponent fiber 20 can include more than two (e.g., any number from three to ten) domains.

As illustrated in FIG. 2, first polymer domain 22 is configured as a core and second polymer domain 24 is configured a sheath, which substantially surrounds first polymer domain 22. In some embodiments, a multicomponent fiber can also include two or more polymer domains in a different arrangement (e.g., in a side-by-side arrangement, in a pie arrangement, or in an "islands-in-the-sea" arrangement). Typically, the cross section of multicomponent fiber 20 having a sheath-core configuration is circular. The first and second polymer domains in such a fiber can be either concentric or acentric (e.g., a configuration in a side-by-side or eccentric multicomponent fiber).

The weight ratio of polymer domains or components in multicomponent fiber 20 can vary as desired. Typically, the weight ratio of first polymer domain 22 to second polymer domain 24 ranges from 90:10 to 10:90 (e.g., from 80:20 to 20:80, or from 75:25 to 65:35 such as 70:30). In some embodiments, the weight ratio of the first and second polymer domains can be outside of the above range.

In general, first polymer domain 22 has a first polymer and second polymer domain 24 has a second polymer different from the first polymer. The term "polymer" mentioned herein includes both homopolymers and copolymers (e.g., random copolymers, block copolymers or graft copolymers). A copolymer can include two or more (e.g., any number from three to five) different types of monomer repeat units. A copolymer can also be a terpolymer, which contains three different monomer repeat units. Each of the first and second polymers can independently be an addition polymer such as a polyolefin (e.g., a polyethylene or a polypropylene) or a condensation polymer such as a polyester (e.g., a polylactide). For example, the first polymer can be a polypropylene polymer and the second polymer can be a polyethylene polymer. As another example, the first polymer can be a polylactide polymer and the second polymer can be a polypropylene polymer. The first and second polymers can also be formed from the same monomers, but have different molecular weights, molecular weight distributions, melt flows, or melt indexes. For example, the first polymer can be a polypropylene having a first molecular weight and the second polymer can be a polypropylene having a second molecular weight different from the first molecular weight.

Various types of polyethylene can be used in the first or second polymer domain. As an example, the first or second polymer domain can include a branched (i.e., non-linear) low density polyethylene or a linear low density polyethylene (LLDPE). The polyethylene can be produced from any of the well known processes, including those prepared by using metallocene and Ziegler-Datta catalyst systems. LLDPE is typically produced by a catalytic solution or fluid bed process under conditions established in the art. The resulting polymers are characterized by an essentially linear backbone. The density of LLDPE can be controlled by the amount of one or more comonomers incorporated into the otherwise linear polymer backbone. Various alpha-olefins (e.g., olefins having four to eight carbon atoms) are typically copolymerized with ethylene in producing LLDPE. The alpha-olefins can be present in the polymer in an amount up to about 10 percent by weight. Examples of comonomers for LLDPE include butene, hexene, 4-methyl-1-pentene, and octene. In general, LLDPE can be produced with various density and melt index properties such that the polymer can be suitable for melt-spinning with polypropylene. For example, suitable density values for LLDPE range from 0.87 to 0.96 glee (ASTM D-792) (e.g., 0.90 to 0.945 glee) and melt index values usually range from 0.1 to about 150 g/10 ml (ASTM D1238-89, 190° C.). For spunbonded filaments, the LLDPE typically has a melt index of greater than 10 (e.g., greater than 15 or greater than 25). Examples of commercially available LLDPE polymers include those from Dow Chemical Company, such as ASPUN Type 6811 (27 MI, density: 0.923), Dow ASPUN Type 6835A (17 MI, density: 0.950), Dow ASPUN Type 6850A (30 MI, density: 0.955), Dow LLDPE 2500 (55 MI, density: 0.923), Dow LLDPE Type 6808A (36 MI, density: 0.940), and the EXACT series of LLDPE polymers from Exxon Chemical Company, such as EXACT 2003 (31 MI, density: 0.921).

Various polypropylenes made by processes known in the art (including those prepared by using a metallocene or Ziegler-Natta catalyst system) can also be used in the first or second polymer domain. In general, the polypropylene can be an isotactic or syndiotactic and can be a homopolymer or a copolymer. The polypropylene can have a melt flow rate (MFR) of greater than 5 (e.g., greater than 10, greater than 15, greater than 20, greater than 25, greater than 30, greater than 35, or greater than 65). Examples of commercially available propylene homopolymers include SOLTEX Type 3907 (35 MFR, CR grade), HIMONT Grade X10054-12-1 (65 MFR). Exxon Type 3445 (35 MFR), Exxon Type 3635 (35 MFR) AMOCO Type 10-7956F (35 MFR), Aristech CP 350 J (approximately 35 MFR), and Total PP M3766 (approximately 22 MFR). Examples of commercially available propylene copolymers include Exxon 9355 (i.e., a random propylene copolymer with 3% ethylene having a 35 melt flow rate); Rexene 13S10A (i.e., a random propylene copolymer with 3% ethylene having a 10 melt flow rate); Fina 7525MZ (i.e., a random propylene copolymer with 3% ethylene having an 11 melt flow rate), Montel EPIX 30F (i.e., a random propylene copolymer with 1.7% ethylene having an 8 melt flow rate), and propylene copolymers from the CATALLOY series from Himont.

The first or second polymer domain can include more than one (e.g., any number from two to five) polymers. For example, the first or second polymer domain can include a blend containing a polyolefin and another polymer. Examples of other multicomponent fibers are disclosed in, e.g., U.S. Pat. Nos. 6,420,285, 6,417,122, and 6,417,121.

Multicomponent fiber 20 can be produced by using suitable equipment and processing techniques known in the art. For example, two polymers (e.g., a polypropylene and a polyethylene) can be fed into two extruders in which the polymers are melted and extruded from the extruders. The molten polymers can then be directed into a spinneret with composite spinning orifices for sheath/core, side-by-side or other multicomponent fiber types, spun through this spinneret, quenched, and then attenuated to form multicomponent fibers (e.g., continuous multicomponent fibers). Examples of such an extruding process are disclosed in, e.g., U.S. Pat. Nos. 3,595,731 and 4,770,925.

In some embodiments, a single component, multiconstituent fiber can be used instead of multicomponent fiber 20. The multiconstituent fiber includes a mixture of two or more constituents (e.g., two, three, four, or five different types of polymers). The constituents can be either compatible or incompatible and can be the polymers described above for use in multicomponent fibers. For example, a single component fiber can include a blend of polypropylene and polyethylene. Fabrics containing multiple constituents have been described, for example, in U.S. Pat. No. 5,804,286. In some embodiments, the surface-Modifying composition described above can also be used on a multiple component fiber 20 that contains multiple constituents.

Figure 3:
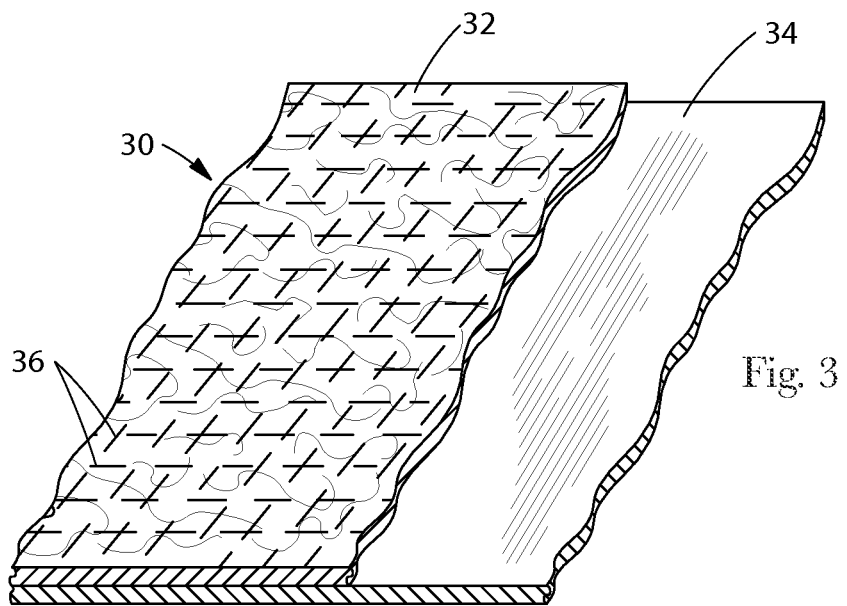
FIG. 3 is a prospective view of a non-woven laminate containing the fabric shown in FIG. 1, with the respective layers being exposed for clarity of illustration.

FIG. 3 is a perspective view of an exemplary laminate 30 containing fabric 10 described above. As used herein, the term "laminate" refers to a structure formed by attaching (e.g., by bonding) a non-woven fabric to one or more additional material layers such as additional non-woven fabrics, other types of fabrics, or films. In this embodiment, laminate 30 is a two-ply (or two-layer) laminate containing ply 32, ply 34, and a plurality of intermittent bonds 36. Ply 32 includes a non-woven fabric 10 (e.g., a spunbonded non-woven fabric) formed of multicomponent fibers, such as fibers 20 described above. Ply 34 can be a composite fabric in any suitable form, such as a meltblown non-woven fabric, a spunbonded non-woven fabric, a fabric of staple fibers, or a film (e.g., an extension film or an elastic film). Although FIG. 3 illustrates a two-ply laminate, one skilled in the art will appreciate that laminate 30 can also include one or more additional plies, which can be the same or different from ply 32 or 34. For example, the laminate can include an additional ply (not shown in FIG. 3) bonded on the surface of ply 34 opposite the surface onto which ply 32 is bonded.

In general, plies 32 and 34 can be bonded and/or laminated by any suitable methods known in the art. Lamination and/or bonding can be achieved, for example, by hydroentanglement of the fibers, spot bonding, through-air bonding, and the like. For example, plies 32 and 34 can be laminated together in a spot bonding process by passing through a heated patterned calender to form discrete thermal point bonds indicated at 36. It is also possible to achieve bonding through the use of an appropriate bonding agent (e.g., an adhesive such as a hot melt adhesive). Spot bonding includes continuous or discontinuous pattern bonding, uniform or random point bonding, or a combination thereof, all of which are well known in the art.

When laminate 30 includes more than two plies, the bonding between the plies can be made after assembly of laminate 30 so as to join all of the plies simultaneously or can be made to join selected plies prior to the final assembly of laminate 30. Various plies can be bonded by different bonding processes in different bonding patterns. In general, laminate bonding can be the same as or different from the process used in individual layer bonding, or can be used in conjunction with individual layer bonding.

Laminates of a spunbonded non-woven fabric made from the multicomponent fibers described above and a fabric or layer of meltblown microfibers can be used as barrier fabrics in medical devices, protective clothing, and hygiene products (e.g., as barrier leg cuffs in diapers).

In some embodiments, a non-woven fabric laminate can be made by combining one or more non-woven spunbonded fabrics 10 with a film (e.g., an extension film or an elastic film), such as a film of a thermoplastic polymer (e.g., a polyolefin). Such a laminate can be used in hygiene products (e.g., as barrier leg cuffs and back sheets in diapers). For example, a non-woven fabric laminate can be made by forming a non-woven spunbonded fabric 10 on the opposite side of an elastic film. The laminate can then be stretched (e.g., by using a ring rolling machine) to form, an elastic diaper component, which can be used as back ears in a diaper, a waist band, or a side panel for a pull on pant diaper. In some embodiments, laminate 30 includes a ply or layer 32 of a non-woven fabric (e.g., a spunbonded non-woven fabric formed of the multicomponent fibers described above) laminated to a film 34 formed of a polyolefin (e.g., a polyethylene). Film 34 can have a thickness of 0.8 to 1 mil (i.e., 20.32 µm to 25.4 µm).

Film 34 can be either a non-breathable or breathable film. As used herein, the term "breathable films" refers to films that provide a barrier to the passage of a liquid (such as water, blood, or urine) yet allow the passage of water in its gaseous state (e.g., water vapor). Films can be rendered breathable during formation of a film (e.g., by adding particulate material such as calcium carbonate to the molten polymer used to produce the film). Such films are commercially available. Films can also be rendered breathable after the formation of a film. For example, breathability can be imparted to a film after lamination of the film to another substrate (e.g., a non-woven fabric described above) and stretching or elongating the laminate (e.g., by mechanical stretching). Such laminates are particularly useful as back sheet components in disposable absorbent articles, such as disposable diapers, medical fabrics (e.g., disposable medical or surgical gowns), and other protective clothing. Examples of breathable films are disclosed in U.S. Pat. No. 5,865,926.

Lamination and/or bonding of the non-woven fabric 32 to the film layer 34 can be achieved by adhesive lamination using a continuous or discontinuous layer of adhesive. This approach can yield a diaper back sheet with superior softness. A suitable adhesive, if desired, can applied either to fabric 32, to film 34, or to both, as either a continuous or discontinuous coating. Where a continuous adhesive coating is employed, the adhesive layer can be relatively thin and sufficiently flexible or extensible to allow fabric 32 and film 34 to elongate upon stretching. Where a discontinuous adhesive is employed, the adhesive can be less extensible and can be in any suitable intermittent pattern (such as lines, spirals, or spots). The adhesive can be applied continuously or intermittently by any accepted method such as spraying, slot coating, or meltblowing.

Suitable adhesives can be made from a variety of materials including polyolefins, polyvinyl acetate, polyamides, hydrocarbon resins, waxes, natural asphalts, styrenic rubbers, and blends thereof. Examples of commercially available adhesives include Century 5227 manufactured by Century Adhesives, Inc. (Columbus, Ohio) and HL-1258 manufactured by H.B. Fuller Company (St. Paul, Minn.).

The non-woven laminate 30 can also be produced by thermal lamination of non-woven fabric 32 to film 34. One advantage of this approach is the elimination of the adhesive, thereby reducing manufacturing costs. It can also be desirable to utilize coextruded films 34 that include a sealing/bonding layer in combination with a polyolefin layer such that, when combined with non-woven fabric 32, the resulting laminate 30 can have a desired softness and good thermal bonding characteristics. The non-woven laminate 30 can also be produced by direct extrusion of film 34 onto non-woven fabric 32.

Film 34 can be a polyolefin film (e.g., an extensible polyolefin film) that is extensible at least 100 percent of its original length. The film can have a basis weight within the range of 10 to 40 grams per square meter. Preferably, the film is of the type that is conventionally used as the impermeable outer component of a disposable diaper.

Layer 34 of laminate 30 can be an elastic layer of various forms including webs of bonded filaments, nets, films, foams, parallel arrays of filaments, and the like. Such structures can be produced by methods known in the art. An "elastic" layer mentioned herein refers to a layer having at least a 75% recovery after a single extension of 10% of the original dimension. Any suitable elastomeric forming resins or blends thereof can be utilized in producing the above structures. Examples of such suitable materials include diblock and triblock copolymers based on polystyrene (S) and/or unsaturated or fully hydrogenated rubber blocks. The rubber blocks can include butadiene (B), isoprene (I), ethylene-butylene (EB), or the hydrogenated version. For example, S-B, S-I, S-EB, S-B-S, S-I-S, and S-EB-S block copolymers can be used to produce a rubber block. Examples of commercially available elastomers include the KRATON polymers sold by Kraton Polymer US, LLC; the VECTOR polymers sold by DEXCO; polyurethane elastomeric materials such as ESTANE sold by B.F. Goodrich Company; polyester elastomers such as HYTREL sold by E.I. Du Pont De Nemours Company; polyetherester elastomeric materials such as ARNITEL sold by Akzo Plastics; and polyetheramide materials such as PEBAX sold by Elf Atochem Company; polyolefin elastomers such as INSITE, AFFINITY, or ENGAGE polyethylene plastomers sold by Dow Chemical; or the EXACT polyethylene plastomers sold by Exxon Chemical. Crosslinked elastomers such as crosslinked urethanes and rubbers can also be employed. Blends of these polymers with other polymers, such as, polyolefins can be used to enhance processing (e.g., decreasing melt viscosity, allowing for lower melt pressures and temperatures, and/or increasing throughput).

In assembling laminate 30, layers 32 and 34 can be provided in an unstretched state from individual supply rolls. If desired, adhesive can then be applied over the surface of layer 32 or 34. Soon after the adhesive is applied, layers 32 and 34 can be subjected to a pressure to form laminate 30 (e.g., by feeding through calender nip rolls). Alternatively, layers 32 and 34 can be bonded by thermal means with or without an adhesive to form laminate 30.

Figure 4:
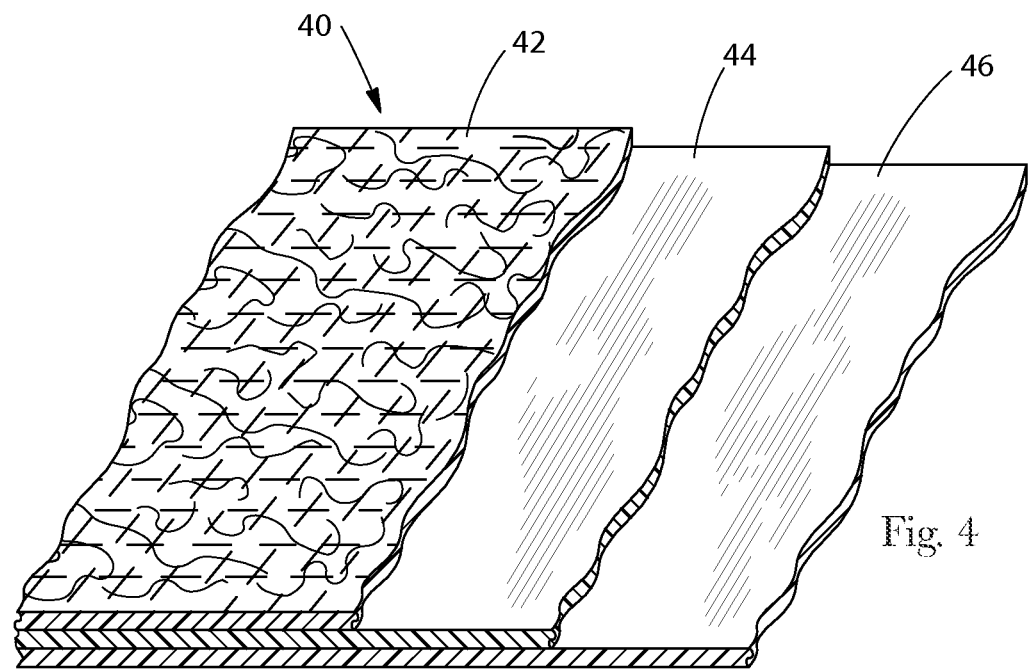
FIG. 4 is a prospective view of a trilayer non-woven laminate containing the fabric shown in FIG. 1.

In some embodiments, laminate 30 can include a third layer on the side of layer 34 opposite layer 32 to form a trilayer laminate. Such a trilayer laminate is shown in FIG. 4. In such embodiments, laminate 40 can include a ply or layer 42 of a non-woven fabric (e.g., a spunbonded non-woven fabric formed of the multicomponent fibers described above) laminated to a layer 44 formed of a polyolefin (e.g., a polyethylene) and a third layer 46 laminated to layer 44 opposite layer 42. This third layer 46 can be either extensible or non-extensible. Any suitable material can be used to form third layer 46. For example, third layer 46 can be formed from a woven or non-woven material, film, or composite (e.g., a film-coated non-woven material). For example, third layer 46 can include a spunbonded non-woven fabric 10 described above. As another example, a thermoplastic polymer (e.g., a polypropylene or polyethylene) film can be used as third layer 46. Commercially available films for third layer 46 include those manufactured by Tredegar Industries, Inc. (Terre Haute, Ind.). If third layer 46 is substantially impervious to liquids, it can be used as a back sheet in disposable personal care products (e.g., diapers, training pants, incontinence briefs, or feminine hygiene products). Any suitable techniques for laminating third layer 46 to layer 44 can be utilized. For example, third layer 46 can be laminated by a thin layer of adhesive in a manner previously described.

In some embodiments, third layer 46 can be a non-woven fabric, which can be extensible or essentially non-extensible. For example, the non-woven fabric can be another fabric formed from multicomponent fibers similar to those used to form fabric 32 so that a non-woven fabric is used on both faces of laminate 30 or 40. In some embodiments, third layer 46 can include an essentially non-extensible non-woven fabric such as a carded thermally point bonded web of low elongation fibers (e.g., Hercules Type 196 polypropylene staple fibers). Typically, layer 42 and layer 46 in laminate 40 include extensible nonwoven fabrics. A preferred extensible nonwoven fabric includes the multicomponent fibers treated with a surface-modifying agent described above. Layer 44 can be an elastic web or film (such as one of the films described above).

Such a laminate 40 are suitable for stretching to provide an elastic laminate useful for diapers, training pant back ears, side panels, or waist bands.

When laminate 30 or 40 is used to produce a personal care product, stretching forces can be applied to laminate 30 or 40 to extend and elongate the laminate in the machine direction (MD) and/or cross-machine direction (CD). As used herein, the term "extensible" refers to a material that can be elongated to at least 110% (e.g., at least 130%, at least 150%, at least 200%, or at least 300%) of its original size in the machine direction or cross-machine direction without breaking when subjected to a tensile test by WSP 110.4. A material that does not meet this definition is considered to be non-extensible. Numerous established techniques can be used in carrying out this operation. For example, to obtain MD elongation in a laminate, one can pass the laminate through two or more sets of nip rolls, each set moving faster than the previous set. CD elongation can be achieved through tentering. Another method of obtaining MD or CD elongation is "ring rolling." Examples of ring rolling process are disclosed in U.S. Pat. No. 5,242,436. Unexpectedly, by applying a composition containing a surface-modifying agent (such as those described above) onto the surface of fabric 32 or 42, laminate 30 or 40 exhibits significantly improved fiber abrasion resistance and reduced fiber breakage or fiber pull-out during stretching (e.g., during a ring rolling process) so that the contamination of the stretching machine (e.g., a ring rolling machine) can be minimized.

Upon application of elongation forces to laminate 30 or 40, fibers within extensible fabric 32 or 42 oriented in the direction of the elongation can experience tension, and the fabric and fibers can undergo deformation. During this process, the fibers are capable of elongating well beyond their unstretched length. As an example, fabric elongation between 70% and 300% (e.g., between 100% and 200%) can be realized. In some embodiments, the fibers can be elongated past their elastic limit, thereby undergoing plastic deformation and becoming permanently elongated. In some embodiments, intermittent bonds distributed throughout layer 32 or 42 can be of high strength such that fibers are sufficiently tied down within layer 32 or 42 and fiber detachment can be reduced during the elongation process.

Laminate 30 or 40 can be particularly well suited for use in various personal care products such as diapers (e.g., pants-type diapers, training pant diapers, tape-type diapers, or mechanical fastener-type diapers), incontinence pads, incontinence briefs, sanitary napkins, bandages, sliding sheets (e.g., for transferring a patient from one bed to another bed), and feminine hygiene products. Since laminate 30 or 40 is both soft and strong, a diaper made from such a laminate can withstand rigorous movement of the wearer without rubbing or chafing the wearer's skin during use.

In some embodiments, fabrics or laminates made according to embodiments of the present disclosure can be incorporated into absorbent articles. An absorbent article can absorb liquid bodily exudates such as sweat, blood, urine, menses, etc. An absorbent article can be a product or a material. Examples of absorbent articles include products and/or materials for sanitary protection, hygienic use, and/or wound care.

Some absorbent articles are disposable. A disposable absorbent article is configured to be partly or wholly disposed of after a single use. A disposable absorbent article is configured such that the soiled article, or a soiled portion of the article, is not intended to be restored and reused (e.g., not intended to be laundered). Examples of disposable absorbent articles include wound care products, such as bandages and dressings, as well as feminine care products, such as pads and liners. Disposable absorbent articles can use embodiments of the present disclosure.

Some absorbent articles are wearable. A wearable absorbent article is configured to be worn on or around a body of a wearer. Wearable absorbent articles can also be disposable. Examples of disposable wearable absorbent articles include disposable diapers and disposable incontinence undergarments. A disposable wearable absorbent article can receive and contain bodily exudates while being worn by a wearer. In some embodiments, a disposable wearable absorbent article can include a topsheet, an absorbent core, an outer cover, a waist opening, and leg openings. Disposable wearable absorbent articles can use embodiments of the present disclosure.

Figure 5:
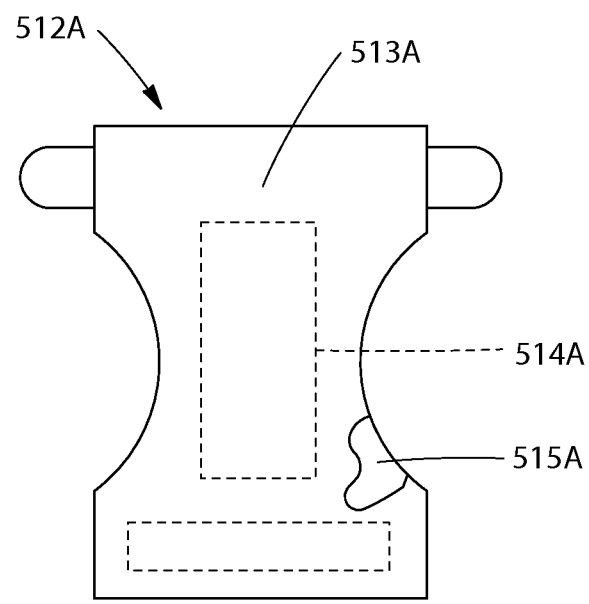
FIG. 5 is an inside plan view illustrating a front-fastenable wearable absorbent article.
Figure 6:
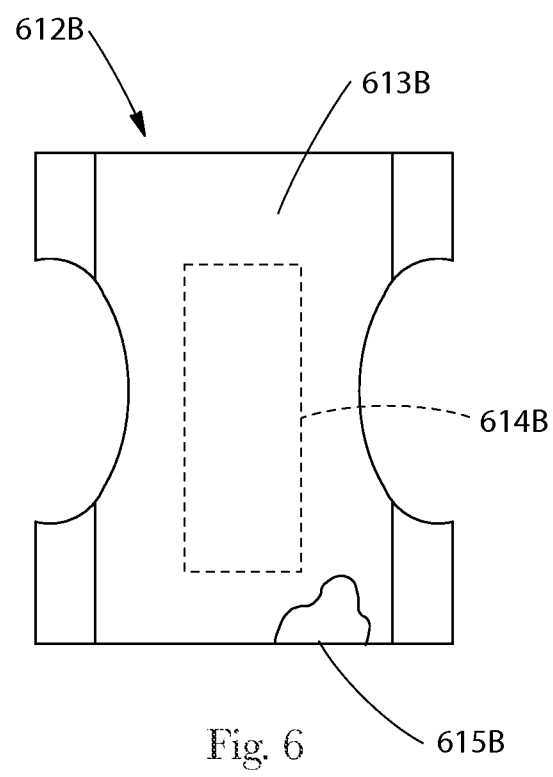
FIG. 6 is an inside plan view illustrating a pant-type wearable absorbent article.
Figure 7:
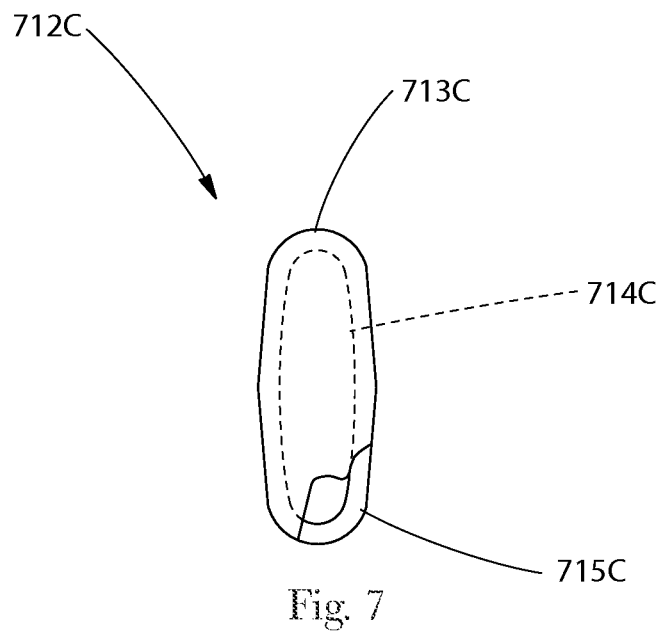
FIG. 7 is an inside plan view illustrating a feminine pad absorbent article.

FIGS. 5-7 illustrate various absorbent articles, with one or more elements made with materials according to embodiments of the present disclosure. For clarity, FIGS. 5-7 do not illustrate all details of the absorbent articles.

FIG. 5 is an inside plan view illustrating a front-fastenable disposable wearable absorbent article 512A. The present disclosure contemplates that, an absorbent article that is configured to be front-fastenable can also be configured to be rear fastenable or side-fastenable, as will be understood by one of ordinary skill in the art.

The front-fastenable wearable absorbent article 512A includes a wearer-facing external surface 513A, a garment-facing external surface 515A, and an absorbent material 514A. The absorbent material 514A is disposed between the wearer-facing external surface 513A and the garment-facing external surface 515A.

The wearer-facing external surface 513A is a layer of one or more materials that form at least a portion of an inside of the front-fastenable wearable absorbent article and faces a wearer when the absorbent article 512A is worn by the wearer. In FIG. 5, a portion of the wearer-facing external surface 513A is illustrated as broken-away, in order to show the garment-facing external surface 515A. A wearer-facing external surface is sometimes referred to as a topsheet. The wearer-facing external surface 513A is configured to be liquid permeable, such that bodily fluids received by the absorbent article 512A can pass through the wearer-facing external surface 513A to the absorbent material 514A. In various embodiments, a wearer-facing external surface can include a nonwoven material and/or other materials.

The absorbent material 514A is disposed subjacent to the wearer-facing external surface 513A and superjacent to the garment-facing external surface 515A, in at least a portion of the absorbent article 512A. In some embodiments, an absorbent material of an absorbent article is part of a structure referred to as an absorbent core. The absorbent material 514A is configured to be liquid absorbent, such that the absorbent material 514A can absorb bodily fluids received by the absorbent article 512A. In various embodiments, an absorbent material can include wood pulp, or super absorbent polymers (SAP), or another kind of absorbent material, or any combinations of any of these materials.

The garment-facing external surface 515A is a layer of one or more materials that form at least a portion of an outside of the front-fastenable wearable absorbent article and faces a wearer's garments when the absorbent article 512A is worn by the wearer. A garment-facing external surface is sometimes referred to as a backsheet. The garment-facing external surface 515A is configured to be liquid impermeable, such that bodily fluids received by the absorbent article 512A cannot pass through the garment-facing external surface 513A. In various embodiments, a garment-facing external surface 513A can include a non-woven fabric or laminate described herein. In other embodiments, a garment-facing external surface 513A can include a film and/or other materials.

The front-fastenable wearable absorbent article 512A also includes extensible side ears, configured to stretch around the sides of a wearer when the article 512A is worn. The extensible side ears also include a fastener, to fasten the back of the article to the front. Each of the extensible side ears can be formed of any of the embodiments of a laminate, as described herein. As a first example, a side ear can be formed of a nonwoven-film laminate that is incrementally stretched. As a second example, a side ear can be formed of a nonwoven-film-nonwoven laminate that is incrementally stretched. In either of these examples, additional materials can be added, and additional processing can be employed.

FIG. 6 is an inside plan view illustrating a pant-type disposable wearable absorbent article 612B. The present disclosure contemplates that, an absorbent article that is configured to be pant type can be configured to be side-fastenable or without fasteners, as will be understood by one of ordinary skill in the art.

The pant-type wearable absorbent article 612B includes a wearer-facing external surface 613B, a garment-facing external surface 615B, and an absorbent material 614B, which are each generally configured in the same manner as the like-numbered element in the embodiment of FIG. 5. The pant-type wearable absorbent article 612B also includes extensible side panels, configured to stretch around the sides of a wearer when the article 612B is worn. The extensible side panels may or may not include a fastener, to fasten the back of the article to the front. Each of the extensible side panels can be formed of any of the embodiments of a laminate, as described herein. As a first example, a side panel can be formed of a nonwoven-film laminate that is incrementally stretched. As a second example, a side panel can be formed of a nonwoven-film-nonwoven laminate that is incrementally stretched. In either of these examples, additional materials can be added, and additional processing can be employed.

FIG. 7 is an inside plan view illustrating a disposable feminine pad absorbent article 712C. The feminine pad absorbent article 712C includes a wearer-facing external surface 713C, a garment-facing external surface 715C, and an absorbent material 714C, which are each configured in a manner similar to the like-numbered element in the embodiments of FIGS. 5 and 6.

Figure 8:
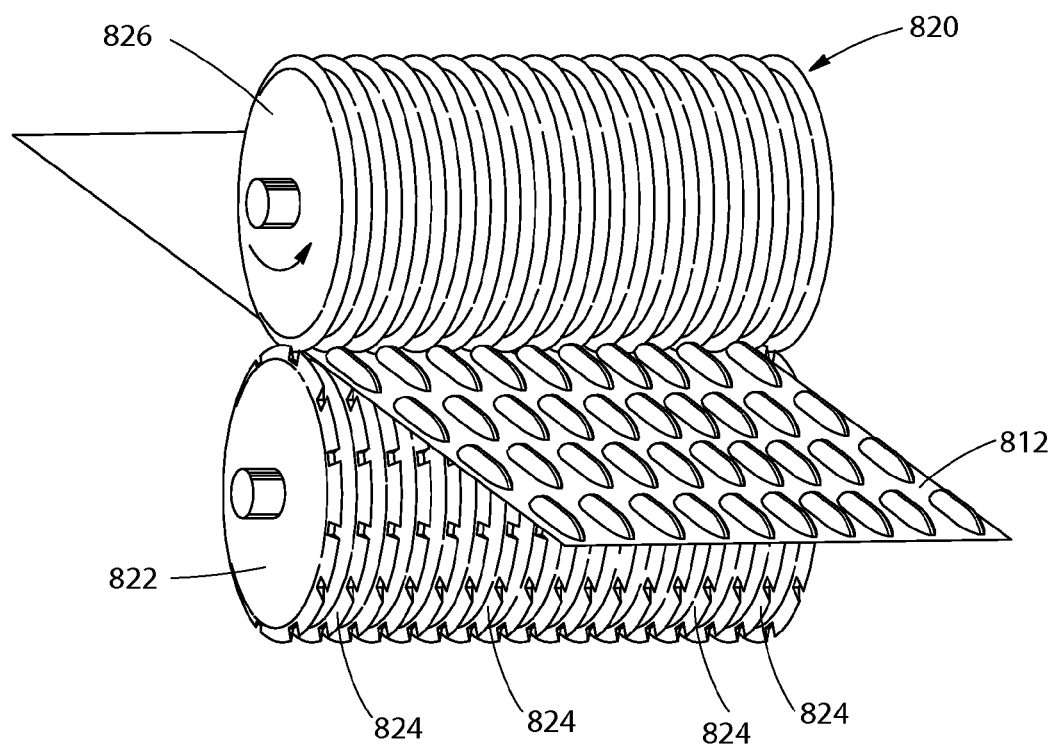
FIG. 8 illustrates an exemplary ring-rolling apparatus.

FIG. 8 illustrates an exemplary ring-rolling apparatus 820 used to incrementally stretch a web of nonwoven material 812 of the present disclosure. The apparatus 820 includes a patterned roll 822, including raised elements or teeth 824, and a non-patterned, grooved roll 826. The teeth 824 stretch the web of nonwoven material 812. It is contemplated that a web of nonwoven fabric or laminate of the present disclosure can also be incrementally stretched using variations of the ring-rolling apparatus 820 and/or one or more other kinds of stretching apparatus.

Embodiments of the present disclosure can be used to provide a nonwoven web with a coating that allows for contamination free processing during activation (e.g. incremental stretching) of film non-woven laminates. Also, embodiments of the present disclosure can be understood as a process of continuous application of a glue release agent onto activation equipment by means of a self-cleaning, coated nonwoven that remains fully functional as part of an activated stretch panel laminate. Further, embodiments of the present disclosure can be understood as a functional stretch laminate nonwoven substrate that acts as glue release applicator and glue removal wipe for contamination-free processing. The functionality of this material can be determined by measuring and evaluating creep, glue bond strength, holes in film, etc. The following example is illustrative and not intended to be limiting. The contents of all publications cited herein (e.g., patents, patent application publications, and articles) are hereby incorporated by reference in their entirety.

EXAMPLES

Preparation of Spunbonded Bicomponent Fabrics

The following spunbonded bicomponent fabrics were made by treating their surfaces with a surface-modifying agent: (1) x460109 (which was treated with surface-modifying agent A), (2) x400109 (which was treated with surface-modifying agent B), (3) remakes of x460109 and x400109, and (4) x340109 (which was treated with a surface-modifying agent). In addition, fabrics (i.e., x350109 and 065RXJO09P) not treated with a surface-modifying agent were prepared and used as a comparison. X350109 was prepared in the same manner as that used to prepare the other fabric examples except that it was not treated with a surface-modifying agent, 065RXJO09P was prepared in the same manner as that used to prepare x350109 except it was bonded using a temperature 15-20° C. lower than that used to form x350109.

These spunbonded bicomponent fabrics were produced on a commercial scale Reicofil-3 type production line similar to the machines currently offered for sale by the Reifenhauser Company Machinenfabrik in Troisdorf, Germany (see, e.g., U.S. Pat. Nos. 5,162,074; 5,344,297; 5,466,410; and 5,814,349). The bicomponent fabrics were made using Dow 6850A LLDPE (30 MI, density: 0.955) as the sheath polymer and Total polypropylene M3766 (approximately 22 MFR) as the core polymer. The weight ratio of the sheath and core was about 30/70. The core also contained approximately 0.3% by weight of $TiO_2$. Specifically, the spunbonded bicomponent fabrics were produced by melting the sheath and core polymers in two different extruders, conveying the molten polymers to a spin bank or spin beam assembly (which included a spinneret plate and a distribution plate) connected to the extruders for separately receiving the molten sheath and core polymers, combining the polymers at the spinneret orifices to form a curtain of multicomponent fibers, quenching the fibers with cool air as they exited as a full width curtain of fibers, attenuating the fibers in the curtain, depositing the curtain (or multiple curtains depending on the number of spin beams) of attenuated fibers via a filament depositing unit (a diffuser) on a moving wire, and then bonding the resulting web of fibers to yield a non-woven fabric.

To make the fabrics listed in Table 1, special attention was given to bonding the web of spunbonded bicomponent fibers. An embossed calender pattern was used that bonded approximately 25-30% of the surface of the non-woven fabric. The calender temperature and fabric speed were carefully selected so as to bond the webs at the maximum temperature possible without the bicomponent web sticking to the calender surface. While the calender temperature was not directly measured, the temperature of the hot oil circulating within the embossing and smooth rolls of the calender was significantly higher than the melting temperature of the polyethylene sheath polymer. Thus, it was important to utilize an embossed roll coated with an anti-stick formulation generally similar to the anti-stick coating described in European Patent EP 1,432,860.

The fabrics thus formed were treated with a surface-modifying agent. Two different surface-modifying agents were used. Agent A, i.e., Silwet L-7602 (Momentive Performance Materials, Albany, N.Y.), was used to prepare x460109 and its remake. Agent B, i.e., Lurol 3503 (Goulston Technologies, Monroe, N.C.), was used to prepare x400019 and its remake. In addition, a surface-modifying agent, i.e., Nuwet 237 (a siloxane polymer available from Momentive Performance Materials, Albany, N.Y.), was used to prepare x340109. Specifically, the surface-modifying agents were added to water to form a diluted solution or emulsion, and were then applied to the surface of the fabrics formed above by using a kiss roll. The surface-treated fabrics were then dried to remove the water. The percentages of a surface-modifying agent in a dried form in the total weight of the fabrics are summarized in Table 1.

The fabrics thus formed were made using a three beam spunbonding machine and therefore formed a SSS type of structure. The fabrics had basis weights of 22.0 g/m$^2$. The fibers showed an average linear mass density in the range of approximately 2.0-2.6 denier per filament, which was achieved by balancing various factors such as the polymer through-put (grams/minute/hole), polymer melt temperature, quench temperature, and attenuation cabin pressure.

The properties of these fabrics were measured and are summarized in Table 1 below.

Mechanical Properties—CD and MD Tensile Strength and Elongation

CD and MD tensile strength and elongation values for the fabrics prepared above were measured using 50 mm wide fabric stripes with gauge length of 100 mm and a cross head speed of 100 mm/minute according to EDANA method 20.2-89 or WSP 110.4. The results showed that the CD elongation values for these fabrics were all greater than 70% and therefore exhibited high extensibility. In addition, the CD tensile strength values were all less than 3 N/cm. When these fabrics were combined with an extensible film or an elastic film, the resulting laminates were able to survive stretching via ring rolling.

Sutherland Ink Rub Test

As another example, the abrasion resistance of these fabrics was measured by using the Sutherland Ink Rub test. The test was performed generally following ASTM method 5264 except that 320 grit sandpaper and an one pound weight were used. Specifically, after a surface of a fabric test sample was abraded by rubbing for 20 cycles at a rate of 42 cycles/minute, a fiber removal tape (a polymask protection tape sold by 3M as part number 3126) was held against the fabric test sample for 20 seconds under a weight of 2,200 grams. The fiber removal tape was weighted before and after application to the abraded surface. The change in weight was recorded to give the weight of fuzz removed from the abraded test sample. Five specimens of each fabric candidate were abraded to allow an average to be generated.

The Sutherland Ink Rub test used a sample size of 11.0 cm×4.0 cm and therefore had a 44 cm$^2$ area in contact with the sandpaper. The weight loss measured by the test was reported as mg/cm$^2$. A 27 g/m$^2$ high extension carded (HEC) fabric sample (Fiberweb, Simpsonville, S.C.) was used as a control sample. The control sample (5 specimens) was abraded with each set of fabric candidates in order to obtain the correlation factor needed for the calculation of the Ink Rub Test result. The correlation factor was needed to account for differences in results due to lot to lot changes in the sandpaper. As specified in the ASTM test method, the final Ink Rub Result was calculated based on this correlation factor and the actual measured weight loss of the fabric The Sutherland Ink Rub test results showed that the weight losses on both the embossed side and the smooth side of the tested fabrics were less than 0.1000 mg/cm$^2$.

Preparation of Laminates Using the Fabrics Prepared Above

The fabrics prepared above were laminated to two sides of an elastic film by using a hot melt adhesive on a pilot line. Each resultant laminate was then stretched via ring rolling to yield an elastic laminate. After the ring rolling was continued for a specified period of time, the process was stopped and the surface of the ring roll was examined to see whether any adhesive and/or fabric debris had been deposited on the ring roll surface. The results are summarized in Table 1.

As shown in Table 1, the ring rolls used to stretch fabrics x460109 and x400109 (which were treated with agents A and B, respectively) were almost not contaminated with any adhesive or fabric debris after 60-100 minutes of ring rolling. By contrast, the ring roll used to stretch fabric x350109 (which was not treated with a surface-modifying agent) was contaminated with a significant amount of adhesives and fabric debris.

Preparation of Diapers Using the Laminates Prepared Above

The above lamination and ring rolling process was repeated as part of the integrated process of making pant-type baby diapers using fabrics x460109 and x400109. After an extended period of time (e.g., 1-2 hours) of stretching using a ring roll in a diaper machine, the ring roll was examined for evidence of contamination from adhesives or fiber debris.

As shown in Table 1, when fabrics x460109 and x400109 were used to make diapers, the contamination level on the ring roll was sufficiently low such that the diaper making process could continue for an extended period of time (i.e., up to 2 hours) without the need of cleaning. By contrast, when a fabric similar to fabric x350109 (which was not treated with a surface-modifying agent described above) was used to make diapers, the diaper making process had to be stopped after less than 5 minutes to clean the contamination built up on the ring roll. As a result, this fabric would not be feasible for use in commercial manufacturing of diapers.

TABLE 1

| Trial Number | Agent | Agent Level as wt % | Preliminary Docking Station Results | CD Elongation Results (%) | MD Elongation Results (%) | CD Tensile Strength (N/cm) | MD Tensile Strength (N/cm) | Ink Rub Embossed Side Average (mg/cm$^2$) | Ink Rub Smooth Side Average (mg/cm$^2$) |
|---|---|---|---|---|---|---|---|---|---|
| Remake x400109 | B | 0.04% | Diapers made in a continuous 2 hour trial. Low contamination | 108.55 | 60.03 | 2.13 | 4.44 | 0.0819 ± 0.0150 | 0.0651 ± 0.0090 |
| Remake x460109 | A | 0.02% | Diapers made in a continuous 2 hour trial. | 84.48 | 39.37 | 2.13 | 4.28 | 0.0855 ± 0.0080 | 0.0708 ± 0.0120 |

TABLE 1-continued

| Trial Number | Agent | Agent Level as wt % | Preliminary Docking Station Results | CD Elongation Results (%) | MD Elongation Results (%) | CD Tensile Strength (N/cm) | MD Tensile Strength (N/cm) | Ink Rub Embossed Side Average (mg/cm$^2$) | Ink Rub Smooth Side Average (mg/cm$^2$) |
|---|---|---|---|---|---|---|---|---|---|
| X350109 | None | None | Low contamination Pilot line ran 52 minutes. Significant fiber and adhesive contamination observed | 84.38 | 35.9 | 2.13 | 3.99 | 0.0813 ± 0.016 | 0.0612 ± 0.013 |
| X400109 | B | 0.04% | Pilot line ran 60 minutes, Nearly no contamination | 83.42 | 42.31 | 2.13 | 4.23 | 0.0615 ± 0.0060 | 0.0531 ± 0.0081 |
| X460109 | A | 0.02% | Pilot line ran 100 minutes. Nearly no contamination | 92.48 | 51.47 | 2.23 | 4.30 | 0.0765 ± 0.0060 | 0.0744 ± 0.0050 |
| X340109 | Nuwet 237 | 0.40% | Pilot line ran for extended time. Nearly no contamination observed | 109.72 | 53.75 | 2.48 | 4.56 | 0.0774 ± 0.0090 | 0.0804 ± 0.0070 |
| 065RXJO09P | None | None | Pilot line ran for 15 mins before stop due to contamination | 160 | 114 | 3.09 | 5.53 | 0.1359 ± 0.023 | 0.1380 ± 0.042 |

Shear-Hang Time Test

The Shear Hang Time Test is performed on laminates of the present disclosure. The Shear Hang Time Test can be used for a side ear of a fastenable disposable wearable absorbent article or for a side panel of pant-type disposable wearable absorbent article. The Shear Hang Time Test of the present disclosure is not suitable for other elements of a disposable wearable absorbent article. The object of the Shear Hang Time Test is to determine whether or not a laminate will fail in shear mode within a specified period of time. Thus, the Shear Hang Time Test evaluates the strength of the attachment between the layers of the laminate, when the laminate is subjected to a constant shear stress.

If the laminate is a side ear of a fastenable disposable wearable absorbent article, then the side ear is removed from the article by cutting completely through and all around the portion of the chassis that is adjacent to the side ear. The cut is offset from the location(s) at which the side ear is attached to the chassis. The cut is offset by a constant distance of about 10 mm. The material of the side ear is not cut during removal. Do not stretch the side ear during removal. The side ear is also completely unfastened from the article during removal. The removed side ear and the portions of the cut chassis (that remain attached to the side ear) become a test sample for the Shear Hang Time Test.

If the laminate is a side panel of a pant-type disposable wearable absorbent article, then the side panel is removed from the article by cutting completely through and all around the portion of the chassis that is adjacent to the front of the side panel and by cutting completely through and all around the portion of the chassis that is adjacent to the back of the side panel. Each of the cuts is offset from the location(s) at which the side panel is attached to the chassis. The cut is offset by a constant distance of about 10 mm. The material of the side panel is not cut during removal. Do not stretch the side panel during removal. If the side panel includes a seam between the front of the side panel and the back of the side panel, then the seam is left intact during removal. If the side panel includes a fastener between the front of the side panel and the back of the side panel, then the fastener should be fully fastened (joining the front and the back of the side panel) after removal. The removed side panel and the portions of the cut chassis (that remain attached to the side panel) become a test sample for the Shear Hang Time Test.

In the Shear Hang Time Test, a test sample is secured on one side in a suspended position so that the sample hangs vertically. To the unsecured side of the test sample, a shear stress equivalent to an evenly distributed stress exerted by a 500-gram weight is applied evenly across the width of the test sample. If the layers of the laminate delaminate from each other during a specified period of time, then the test sample is deemed to fail the Shear Hang Time Test. If the layers of the laminate do not delaminate from each other during a specified period of time, then the test sample is deemed to pass the Shear Hang Time Test. The Shear Hang Time test is conducted in a closed and controlled environment at 37.8°±2° C. and 50%±2% relative humidity.

Success criteria for the Shear Hang Time Test is zero failures within an acceptance sampling frequency as dictated by ANSI ASQC Z1.4 (1993) for a criticality factor of 2. Thus, the level of coating applied must be sufficient enough to prevent buildup/contamination on the converting equipment but low enough so as to prevent interference with chemical/mechanical bonding/adhesion when integrated into the finished product, as measured by the shear hang time.

Table 2, as shown below, includes test results for a pant diaper product comprised of a non-woven fabric treated with a surface-modifying agent, as described herein, and then subjected to a Shear Hang Time test.

TABLE 2

| Trial Number | Agent | Agent Level as wt % | Shear Hang Time Results Pass > 120 min |
|---|---|---|---|
| X350109 | None | None | Pass = 0% FAIL (0/47) |
| Remake x460109 | A | 0.02% | Pass = 0% FAIL (0/78) |
| Remake x400109 | B | 0.04% | Pass = 0% FAIL (0/68) |
| X340109 | Nuwet 237 | 0.40% | FAIL = 95% FAIL (19/20) |

Side Creep Test

Table 3, as shown below, includes test results for a pant diaper product comprised of a non-woven fabric treated with a surface-modifying agent, as described herein, and then subjected to a Side Creep test. As used herein, a Side Creep test refers to the measure of a distance that a stretch laminate side portion (side ear or side panel) of a diaper, which has been mechanically and chemically (with adhesive) bonded to the central chassis portion of the diaper at two points (front and rear), delaminates/migrates from the central chassis after the finished product has been applied in use for two hours in a closed and controlled environment at 37.8° C.±2° C. and 50%±2% relative humidity. The Side Creep test has been found to be a very reliable predictor of bond security between the stretch side panel area and central chassis portion of the pant diaper in use. The object of the Side Creep test test is to measure how far the side panel area migrates away from the central chassis of the pant diaper upon delamination given stress in the shear mode in use. Thus, the Side Creep test test evaluates the adhesive and mechanical bond's security, durability, under constant shear stress.

Success criteria for this validated test method is such that the creep test is that: 1) there is no more than a specified distance of delamination/migration between the stretch laminate side and central chassis portions of the diaper; 2) zero failures within an acceptance sampling frequency as dictated by ANSI ASQC Z1.4 (1993) for a criticality factor of 2. Thus, the level of coating applied should be sufficient enough to prevent buildup/contamination on the converting equipment but low enough so as to prevent interference with chemical/mechanical bonding/adhesion when integrated into the finished product, as measured by the side creep.

TABLE 3

| Trial Number | Agent | Agent Level as wt % | Side Panel Creep Results >9 mm = FAIL |
|---|---|---|---|
| x350109 | None | None | Pass = 0% FAIL (0/144) |
| Remake x460109 | A | 0.02% | Pass = 0% FAIL (0/92) |
| Remake x400109 | B | 0.04% | Pass = 0% FAIL (0/196) |
| X340109 | Nuwet 237 | 0.40% | FAIL (5/48) |

The compositions, products and methods of the appended claims are not limited in scope by the specific compositions, products and methods described herein, which are intended as illustrations of a few aspects of the claims and any compositions, products and methods that are functionally equivalent are intended to fall within the scope of the claims. Various modifications of the compositions, products and methods in addition to those shown and described herein are intended to fall within the scope of the appended claims. Further, while only certain representative compositions, products and method steps disclosed herein are specifically described, other combinations of the compositions, products and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

All publications, patent applications, patents, and other references mentioned herein are incorporated by reference herein in their entirety.

What is claimed is:

1. A method of processing a web of laminate, the method comprising:
   providing the web of laminate, wherein the laminate includes at least a layer of nonwoven material attached to a layer of film, and wherein the nonwoven material comprises a fibrous material;
   treating at least a portion of a surface of the fibrous material with a surface-modifying composition, to form a treated laminate;
   providing a machine part with a contact surface;
   contacting the contact surface of the machine part with the fibrous material;
   continuously transferring at least a portion of the surface-modifying agent from the surface of the layer of nonwoven material to the contact surface of the machine part;
   coating at least a portion of the contact surface of the machine part with the surface-modifying composition; and
   incrementally stretching the treated laminate to form an incrementally stretched laminate.

2. The method of claim 1, wherein the providing includes providing the web of laminate, wherein the only fibrous material in the laminate is the layer of nonwoven material, and the nonwoven material is a spunbond nonwoven.

3. The method of claim 1, wherein the providing includes providing the web of laminate, wherein a layer of the fibrous material is adhesively bonded to the layer of film.

4. The method of claim 1, wherein the providing includes providing the web of laminate, wherein the layer of fibrous material is a first layer of nonwoven material, the first layer of nonwoven material is attached to a first side of the layer of film, and the laminate also includes a second layer of nonwoven material attached to a second side of the layer of film.

5. The method of claim 1, wherein the treating includes treating at least a plurality of separate portions of the surface of the fibrous material with the surface-modifying composition, to form the treated laminate.

6. The method of claim 1, wherein the treating includes treating substantially all of the surface of the fibrous material with the surface-modifying composition, to form the treated laminate.

7. The method of claim 1, wherein the treating includes applying the surface-modifying composition directly to the fibrous material.

8. The method of claim 1, wherein the treating includes spraying the surface-modifying composition onto the fibrous material.

9. The method of claim 1, wherein the treating includes treating at least the portion of the fibrous material with the surface-modifying composition to form a treated portion of the fibrous material of the treated laminate, wherein, in the treated portion, the surface modifying composition forms a percentage of a total mass of the treated portion of the fibrous material, and wherein the percentage is greater than or equal to 0.01% and less than or equal to 0.5%.

10. The method of claim 9, wherein the treating includes treating at least the portion of the fibrous material with the surface-modifying composition to form the treated portion of the fibrous material, wherein the percentage is greater than or equal to 0.045%.

11. The method of claim 10, wherein the treating includes treating at least the portion of the fibrous material with the surface-modifying composition to form the treated portion of the fibrous material, wherein the percentage is greater than or equal to 0.125%.

12. The method of claim 9, wherein the treating includes treating at least the portion of the fibrous material with the surface-modifying composition to form the treated portion of the fibrous material, wherein the percentage is less than or equal to 0.335%.

13. The method of claim 12, wherein the treating includes treating at least the portion of the fibrous material with the surface-modifying composition to form the treated portion of the fibrous material, wherein the percentage is less than or equal to 0.18%.

14. The method of claim 1, wherein the treating includes treating at least the portion of the fibrous material with the surface-modifying composition, which includes a surface-modifying agent, which forms at least 50% of a total mass of the surface-modifying composition.

15. The method of claim 14, wherein the treating includes treating at least the portion of the fibrous material with the surface-modifying composition, which includes a surface-modifying agent, which forms at least 75% of a total mass of the surface-modifying composition.

16. The method of claim 1, wherein the treating includes treating at least the portion of the fibrous material with the surface-modifying composition, which includes a surface-modifying agent, which includes a silicone.

17. The method of claim 16, wherein the treating includes treating at least the portion of the fibrous material with the surface-modifying composition, which includes the surface-modifying agent, which includes a polysiloxane.

18. The method of claim 1, wherein the treating includes treating at least the portion of the fibrous material with the surface-modifying composition, which includes a surface-modifying agent, which includes an unsaturated fatty acid.

19. The method of claim 18, wherein the treating includes treating at least the portion of the fibrous material with the surface-modifying composition, which includes the surface-modifying agent, which includes ricinoleic acid.

20. The method of claim 1, further comprising providing an incremental stretching apparatus, which includes ring-rolls, and wherein:
the treating includes coating at least a portion of the ring-rolls with the surface-modifying composition, to form coated ring-rolls; and
the incremental stretching of the treated laminate includes incrementally stretching the treated laminate with the coated ring rolls to form an incrementally stretched laminate.

21. The method of claim 1, further comprising transforming the treated laminate, by using one or more processes, selected from the group, including:
bonding;
cutting;
embossing;
folding; and
seaming.

22. The method of claim 1, further comprising providing an incremental stretching apparatus, which includes ring-rolls, and wherein the incremental stretching of the treated laminate includes incrementally stretching the treated laminate for at least 60 minutes without contaminating the ring-rolls with fibers from the laminate.

23. The method of claim 1, further comprising providing an incremental stretching apparatus, which includes ring-rolls, and wherein the incremental stretching of the treated laminate includes incrementally stretching the treated laminate for at least 100 minutes without contaminating the ring-rolls with fibers from the laminate.

24. A laminate, comprising a layer of nonwoven material attached by an adhesive to a layer of film, wherein at least a portion of a surface of the layer of nonwoven material is treated with a surface-modifying composition and the laminate is incrementally stretched, and wherein, in the portion, the surface modifying composition forms a percentage of a total mass of the nonwoven material, and the percentage is greater than or equal to 0.01% and less than or equal to 0.5%, and wherein when the laminate is subjected to the Sutherland Ink Rub test, the nonwoven material has a weight loss that is less than 0.1 mg/cm$^2$, and wherein at least a portion the surface-modifying agent is configured to be transferred from the surface of the layer of non-woven material, and wherein the surface-modifying agent prevents migration of the adhesive from the surface of the layer of non-woven material.

25. The laminate of claim 24, wherein the only fibrous material in the laminate is the layer of nonwoven material, and the nonwoven material is a spunbond nonwoven.

26. The laminate of claim 24, wherein the layer of nonwoven material is a first layer of nonwoven material attached to a first side of the layer of film, and the laminate also includes a second layer of nonwoven material attached to a second side of the layer of film.

27. The laminate of claim 24, wherein a plurality of separate portions of a surface of the layer of nonwoven material is treated with the surface-modifying composition.

28. The laminate of claim 24, wherein substantially all of a surface of the layer of nonwoven material is treated with the surface-modifying composition.

29. The laminate of claim 24, wherein the percentage is greater than or equal to 0.045%.

30. The laminate of claim 29, wherein the percentage is greater than or equal to 0.125%.

31. The laminate of claim 24, wherein the percentage is less than or equal to 0.335%.

32. The laminate of claim 31, wherein the percentage is less than or equal to 0.18%.

33. The laminate of claim 24, wherein the surface-modifying composition includes a surface-modifying agent, which includes a silicone.

34. The laminate of claim 33, wherein the silicone is a polysiloxane.

35. The laminate of claim 24, wherein the surface-modifying composition includes a surface-modifying agent, which includes an unsaturated fatty acid.

36. The laminate of claim 35, wherein the unsaturated fatty acid is a ricinoleic acid.

37. The article of claim 35, which the laminate is included in an element of the article, and the element is selected from the group including a side ear and a side panel.

38. The article of claim 37, wherein the laminate passes the Shear Hang Time Test for at least 60 minutes.

39. The laminate of claim 37, wherein the laminate passes the Shear Hang Time Test for at least 120 minutes.

40. The article of claim 37, wherein when the laminate is subjected to the Side Creep test, the laminate has a creep of 12 millimeters or less.

41. The article of claim 37, wherein when the laminate is subjected to the Side Creep test, the laminate has a creep of 9 millimeters or less.

42. The article of claim 37, wherein when the laminate is subjected to the Sutherland Ink Rub test, the nonwoven material has a weight loss that is less than or equal to 0.05 mg/cm$^2$.

43. The article of claim 37, wherein when the laminate has an air permeability that is greater than or equal to 90 meters per minute and less than or equal to 200 meters per minute.

44. The article of claim 37, wherein when the laminate has an air permeability that is greater than or equal to 130 meters per minute and less than or equal to 200 meters per minute.

45. A disposable wearable absorbent article, comprising the laminate of claim 24.

46. The article of claim 45, comprising a backsheet that includes the laminate.

\* \* \* \* \*